US012430759B2

(12) United States Patent
Sakamoto et al.

(10) Patent No.: US 12,430,759 B2
(45) Date of Patent: Sep. 30, 2025

(54) IMAGE PROCESSING DEVICE, IMAGE PROCESSING SYSTEM, IMAGE DISPLAY METHOD, AND IMAGE PROCESSING PROGRAM

(71) Applicants: TERUMO KABUSHIKI KAISHA, Tokyo (JP); Rokken Inc., Sakai (JP)

(72) Inventors: Yasukazu Sakamoto, Hiratsuka (JP); Katsuhiko Shimizu, Fujinomiya (JP); Hiroyuki Ishihara, Tokyo (JP); Clément Jacquet, Sakai (JP); Thomas Henn, Sakai (JP); Stephen Tchen, Sakai (JP); Ryosuke Saga, Osaka (JP)

(73) Assignees: Terumo Kabushiki Kaisha, Tokyo (JP); Rokken Inc., Sakai (JP)

( * ) Notice: Subject to any disclaimer, the term of this patent is extended or adjusted under 35 U.S.C. 154(b) by 294 days.

(21) Appl. No.: 17/937,063

(22) Filed: Sep. 30, 2022

(65) Prior Publication Data
US 2023/0025720 A1 Jan. 26, 2023

Related U.S. Application Data

(63) Continuation of application No. PCT/JP2021/011534, filed on Mar. 19, 2021.

(30) Foreign Application Priority Data

Mar. 31, 2020 (JP) ................................ 2020-061800

(51) Int. Cl.
*G06T 7/00* (2017.01)
*G06F 3/14* (2006.01)
(Continued)

(52) U.S. Cl.
CPC .............. *G06T 7/0012* (2013.01); *G06F 3/14* (2013.01); *G06T 7/20* (2013.01); *G06T 7/60* (2013.01);
(Continued)

(58) Field of Classification Search
CPC .......... G06T 7/0012; G06T 7/20; G06T 7/60; G06T 7/70; G06T 15/08;
(Continued)

(56) References Cited

U.S. PATENT DOCUMENTS 6,251,072 B1 6/2001 Ladak et al.
6,385,332 B1 5/2002 Zahalka et al.
(Continued)

FOREIGN PATENT DOCUMENTS

CN 102119848 A 7/2011
CN 103717135 A 4/2014
(Continued)

OTHER PUBLICATIONS

International Search Report (PCT/ISA/210) with English translation and Written Opinion (PCT/ISA/237) mailed on Jun. 8, 2021, by the Japanese Patent Office as the International Searching Authority for International Application No. PCT/JP2021/011534.
(Continued)

*Primary Examiner* — Shefali D Goradia
(74) *Attorney, Agent, or Firm* — Buchanan Ingersoll & Rooney PC

(57) ABSTRACT

An image processing device is an image processing device configured to cause a display to display three-dimensional data as a three-dimensional image, the three-dimensional data representing a biological tissue. The image processing device includes: a control unit configured to detect a series of positions of a catheter inserted into the biological tissue from data obtained in time series by a sensor observing the surrounding of a lumen of the biological tissue while moving in the lumen, and to switch a display mode between a first mode for displaying a first figure representing the series of positions in the three-dimensional image, and a second mode for displaying a second figure representing one posi-
(Continued)

tion among the series of positions in the three-dimensional image.

21 Claims, 15 Drawing Sheets

(51) Int. Cl.
    *G06T 7/20*     (2017.01)
    *G06T 7/60*     (2017.01)
    *G06T 7/70*     (2017.01)
    *G06T 15/08*     (2011.01)
    *G06V 10/56*     (2022.01)
    *G06V 10/74*     (2022.01)

(52) U.S. Cl.
    CPC ............... *G06T 7/70* (2017.01); *G06T 15/08* (2013.01); *G06V 10/56* (2022.01); *G06V 10/761* (2022.01); *G06T 2207/10024* (2013.01); *G06T 2207/10072* (2013.01); *G06T 2207/30021* (2013.01)

(58) Field of Classification Search
    CPC . G06T 2207/10072; G06T 2207/10024; G06T 2207/30021; G06V 10/56; G06V 10/761; G06F 3/14
    See application file for complete search history.

(56) References Cited

U.S. PATENT DOCUMENTS

| | | | |
|---|---|---|---|
| 11,089,351 B2* | 8/2021 | Yoshizawa | G06F 3/011 |
| 11,806,094 B2* | 11/2023 | Sheiner | A61B 34/20 |
| 11,842,456 B2* | 12/2023 | Gluhovsky | G06T 19/00 |
| 2004/0097805 A1* | 5/2004 | Verard | A61B 34/20 |
| | | | 600/428 |
| 2005/0107688 A1* | 5/2005 | Strommer | A61B 5/7475 |
| | | | 600/424 |
| 2005/0288577 A1 | 12/2005 | Weese | |
| 2007/0038081 A1 | 2/2007 | Eck et al. | |
| 2007/0123771 A1* | 5/2007 | Redel | A61B 6/466 |
| | | | 600/407 |
| 2008/0247506 A1* | 10/2008 | Maschke | A61B 6/4476 |
| | | | 378/15 |
| 2010/0215238 A1 | 8/2010 | Lu et al. | |
| 2011/0166418 A1 | 7/2011 | Aoyagi et al. | |
| 2014/0135618 A1 | 5/2014 | Abe et al. | |
| 2015/0223670 A1 | 8/2015 | Fujita et al. | |
| 2015/0320979 A1 | 11/2015 | Fearnot et al. | |
| 2016/0228089 A1* | 8/2016 | Jamello | A61B 8/0883 |
| 2017/0024910 A1 | 1/2017 | Griffin et al. | |
| 2018/0228554 A1* | 8/2018 | Strommer | A61B 5/7289 |
| 2020/0129142 A1* | 4/2020 | Chao | A61B 8/5223 |

FOREIGN PATENT DOCUMENTS

| | | | | |
|---|---|---|---|---|
| JP | H10137238 A | | 5/1998 | |
| JP | 2006508731 A | | 3/2006 | |
| JP | 2007503906 A | | 3/2007 | |
| JP | 2008-113699 A | | 5/2008 | |
| JP | 2011193995 A | | 10/2011 | |
| JP | 2014083289 A | | 5/2014 | |
| JP | 2016516466 A | | 6/2016 | |
| JP | 2017514617 A | | 6/2017 | |
| JP | 2018520839 A | | 8/2018 | |
| WO | WO-2005112750 A1 * | 12/2005 | ......... A61B 18/1492 |
| WO | 2014175853 A1 | | 10/2014 | |
| WO | 2015044983 A1 | | 4/2015 | |
| WO | WO-2018081012 A1 * | 5/2018 | ........... A61B 1/2676 |
| WO | WO-2018200738 A1 * | 11/2018 | ......... A61B 18/1492 |
| WO | 2019/239647 A1 | | 12/2019 | |

OTHER PUBLICATIONS

International Preliminary Report on Patentability (Form PCT/IB/373) and an English Translations of the Written Opinion of the International Searching Authority (Form PCT/ISA/237) issued Sep. 29, 2022, by the International Bureau of WIPO in corresponding International Application No. PCT/JP2021/011534. (8 pages).

Office Action/Search Report (The First Office Action) issued on May 30, 2025, in corresponding Chinese Patent Application No. 202180026956.7 and English translation of the Office Action/Search Report. (14 pages).

* cited by examiner

IMAGE PROCESSING DEVICE, IMAGE PROCESSING SYSTEM, IMAGE DISPLAY METHOD, AND IMAGE PROCESSING PROGRAM

CROSS-REFERENCES TO RELATED APPLICATIONS

This application is a continuation of International Application No. PCT/JP2021/011534 filed on Mar. 19, 2021, which claims priority to Japanese Patent Application No. 2020-061800 filed on Mar. 31, 2020, the entire content of both of which is incorporated herein by reference.

TECHNOLOGICAL FIELD

The present disclosure relates to an image processing device, an image processing system, an image display method, and an image processing program.

BACKGROUND DISCUSSION

U.S. Patent Application Publication No. 2010/0215238, U.S. Pat. Nos. 6,385,332, and 6,251,072 disclose a technique of generating a three-dimensional image of a cardiac cavity or a blood vessel by using an ultrasound (US) image system.

Treatment using intravascular ultrasound (IVUS) is widely executed for a cardiac cavity, a cardiac blood vessel, a lower limb artery region, and the like. IVUS is a device or a method for providing a two-dimensional image of a plane perpendicular to a long axis of a catheter.

At present, an operator needs to execute treatment while reconstructing a three-dimensional structure by stacking the two-dimensional images of IVUS in his/her head, which is a barrier particularly to young doctors or inexperienced doctors. In order to remove such a barrier, it is conceivable to automatically generate a three-dimensional image expressing a structure of a biological tissue such as the cardiac cavity or the blood vessel from the two-dimensional images of IVUS and display the generated three-dimensional image toward the operator. When a catheter for treatment such as ablation is inserted into the biological tissue, it is conceivable to also display the catheter in the three-dimensional image.

It is assumed that a series of positions of the catheter are displayed by using past pull-back information. When a pull-back unit stays at the same place for a certain period of time, there is a case in which almost no relevance is between the series of positions of the catheter extracted from the past pull-back information and a current position of the catheter. In particular, when the catheter is operated while a position of the pull-back unit is fixed, the relevance between the series of past positions and the current position is significantly lost. As a result, the position of the catheter can be difficult to understand.

SUMMARY

The present disclosure facilitates an understanding of a position of a catheter when displaying the catheter in a three-dimensional image of a biological tissue.

An image processing device according to an aspect of the present disclosure is an image processing device configured to cause a display to display three-dimensional data as a three-dimensional image, the three-dimensional data representing a biological tissue. The image processing device includes: a control unit configured to detect a series of positions of a catheter inserted into the biological tissue from data obtained in time series by a sensor observing the surrounding of a lumen of the biological tissue while moving in the lumen, and to switch a display mode between a first mode for displaying a first figure representing the series of positions in the three-dimensional image, and a second mode for displaying a second figure representing one position among the series of positions in the three-dimensional image.

In one embodiment, the control unit is configured to hide the first figure when the display mode is switched from the first mode to the second mode.

In one embodiment, the control unit is configured to display, as the first figure, a linear or tubular figure connecting the series of positions.

In one embodiment, the control unit is configured to display, as the second figure, a spherical figure representing the one position, and display at least one concentric circle or concentric sphere surrounding the spherical figure.

In one embodiment, the control unit is configured to display, as the second figure, a figure in which a thickness dimension on a side near an end of the catheter is larger than a thickness dimension on an opposite side.

In one embodiment, the control unit is configured to display, as the second figure, a bullet-shaped figure representing the one position.

In one embodiment, when displaying a figure representing a position other than a distal end of the catheter as the second figure, the control unit displays the second figure in a color different from that when displaying a figure representing a position of the distal end of the catheter as the second figure.

In one embodiment, the control unit is configured to switch the display mode according to a change in a moving state of the sensor.

In one embodiment, the change in the moving state of the sensor includes a case in which a moving speed of the sensor exceeds a threshold value.

In one embodiment, when the moving speed of the sensor exceeds the threshold value, the control unit switches the display mode according to whether the moving speed of the sensor is equal to or less than an upper limit value.

In one embodiment, the control unit is configured to switch the display mode according to whether the catheter is present in an image plane captured by the sensor.

In one embodiment, when the catheter is present in the image plane, the control unit switches the display mode according to a magnitude of a movement of the catheter in the image plane.

In one embodiment, when the catheter is not present in the image plane, the control unit switches the display mode according to an elapsed time from a time point at which a last position among the series of positions is detected.

In one embodiment, in the second mode, the control unit adjusts at least one of a size or a color of the second figure according to a distance from an inner wall surface of the biological tissue.

In one embodiment, in the second mode, the control unit adjusts at least one of a size or a color of the second figure according to presence or absence of contact with the inner wall surface of the biological tissue.

In one embodiment, in the second mode, the control unit further displays a shadow of the second figure.

In one embodiment, in the second mode, the control unit adjusts an update frequency of the second figure associated with an update of the data.

An image processing system according to an aspect of the present disclosure includes: a sensor configured to acquire tomographic data of the biological tissue while moving in a lumen of the biological tissue; and the image processing device configured to generate the three-dimensional data based on the tomographic data acquired by the sensor.

In one embodiment, the image processing system further includes: the display.

An image display method according to an aspect of the present disclosure is an image display method for causing a display to display three-dimensional data as a three-dimensional image, the three-dimensional data representing a biological tissue. The image display method includes: detecting, by a processor, a series of positions of a catheter inserted into the biological tissue from data obtained in time series by a sensor observing the surrounding of a lumen of the biological tissue while moving in the lumen; and switching, by the processor, a display mode between a first mode for displaying a first figure representing the series of positions in the three-dimensional image, and a second mode for displaying a second figure representing one position among the series of positions in the three-dimensional image.

A non-transitory computer-readable medium (CRM) storing computer program code executed by a computer processor that executes an imaging process comprising: displaying, on a display, three-dimensional data as a three-dimensional image, the three-dimensional data representing a biological tissue; detecting a series of positions of a catheter inserted into the biological tissue from data obtained in time series by a sensor observing the surrounding of a lumen of the biological tissue while moving in the lumen; and switching a display mode between a first mode for displaying a first figure representing the series of positions in the three-dimensional image, and a second mode for displaying a second figure representing one position among the series of positions in the three-dimensional image.

According to the present disclosure, it is possible to facilitate understanding of a position of a catheter when displaying the catheter in a three-dimensional image of a biological tissue.

DETAILED DESCRIPTION

Figure 1:
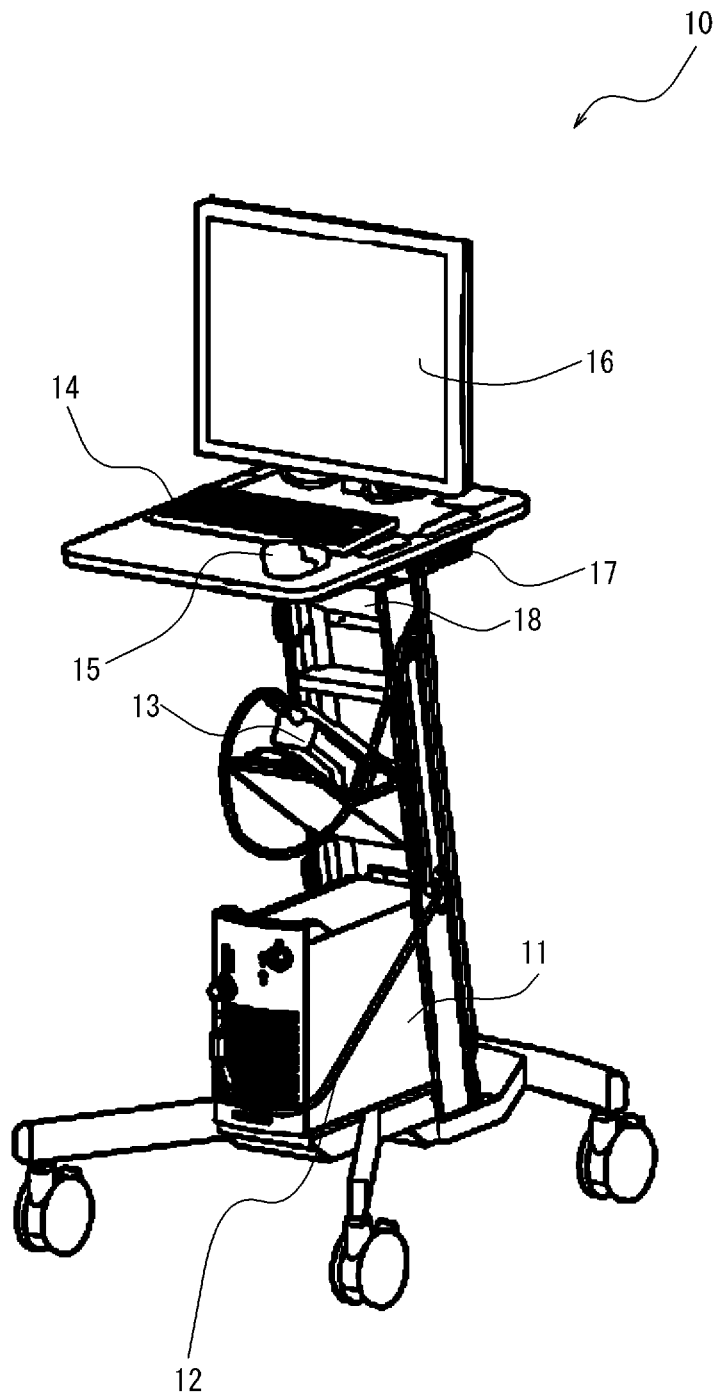
FIG. 1 is a perspective view of an image processing system according to an aspect of the present disclosure.

Set forth below with reference to the accompanying drawings is a detailed description of embodiments of an image processing device, an image processing system, an image display method, and an image processing program. Note that since embodiments described below are preferred specific examples of the present disclosure, although various technically preferable limitations are given, the scope of the present disclosure is not limited to the embodiments unless otherwise specified in the following descriptions.

In the drawings, the same or corresponding parts are denoted by the same reference numerals. In the description of the present embodiment, the description of the same or corresponding parts will be omitted or simplified as appropriate.

An outline of the present embodiment will be described with reference to FIGS. 1, 3, 4, and 5.

An image processing device 11 according to the present embodiment is a computer that causes a display 16 to display three-dimensional data 52 as a three-dimensional image 53, the three-dimensional data 52 representing a biological tissue 60. The image processing device 11 detects a series of positions of a catheter 61 inserted into the biological tissue 60 from data obtained in time series by a sensor observing the surrounding of a lumen of the biological tissue 60 while moving in the lumen. The image processing device 11 switches a display mode between a first mode for displaying a first figure 71 representing the series of positions in the three-dimensional image 53, and a second mode for displaying a second figure 72 representing one position among the series of positions in the three-dimensional image 53.

According to the present embodiment, it is possible to facilitate understanding of a position of the catheter 61 when displaying the catheter 61 in the three-dimensional image 53 of the biological tissue 60. For example, if a user is an operator and operates the catheter 61 while a position of a pull-back unit is fixed, a current position of the catheter 61 is displayed instead of displaying the series of positions of the catheter 61 using past pull-back information. Accordingly, the user can execute treatment without being confused by the past information that does not have relevance to the current position of the catheter 61.

In the present embodiment, an ultrasound transducer 25 is used as the sensor for observing the surrounding while moving in the lumen of the biological tissue 60.

Figure 4:
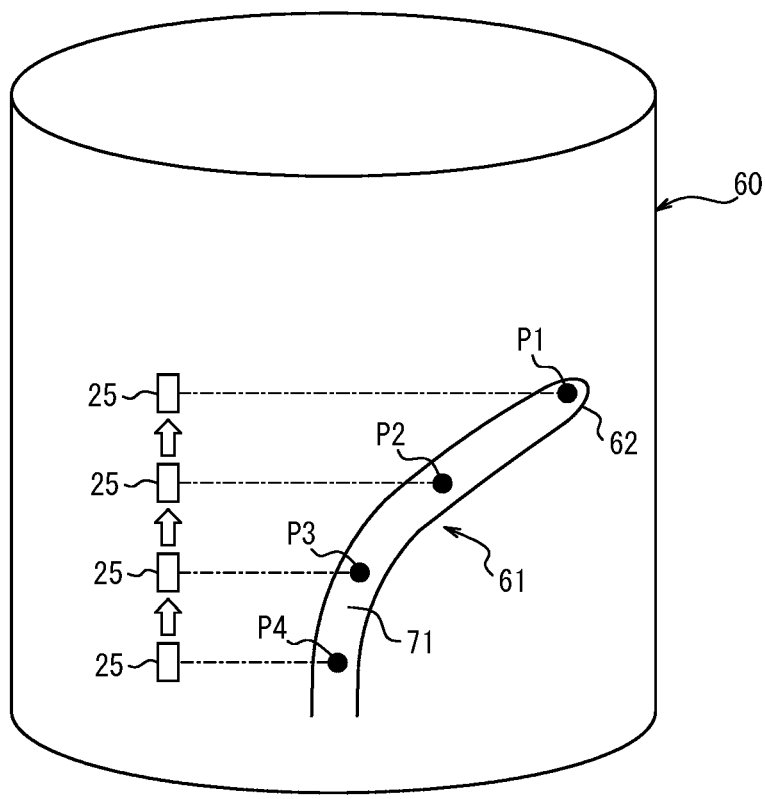
FIG. 4 is a diagram illustrating a three-dimensional image and a first figure displayed in an embodiment.
Figure 5:
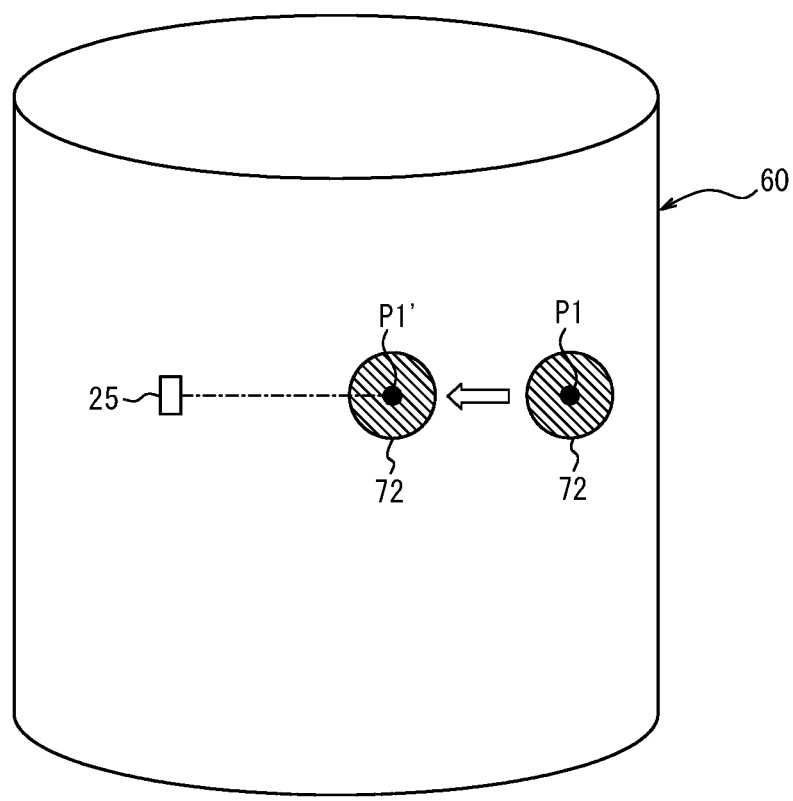
FIG. 5 is a diagram illustrating the three-dimensional image and a second figure displayed in the embodiment.

The biological tissue 60 can be, for example, an organ such as a blood vessel or a heart. In the examples of FIGS. 4 and 5, the biological tissue 60 is a blood vessel.

The catheter 61 can be, for example, an ablation catheter.

In FIGS. 4 and 5, an X-direction and a Y-direction orthogonal to the X-direction correspond to a lateral direction of the biological tissue 60. A Z-direction orthogonal to the X-direction and the Y-direction corresponds to a longitudinal direction of the biological tissue 60.

In the example of FIG. 4, a current display mode is the first mode. By a certain time point T1, a series of positions P1, P2, P3, and P4 of the catheter 61 are detected from the data obtained in time series by the ultrasound transducer 25. The position P1 is a position of a distal end 62 of the catheter 61 at the time point T1. The position P2 is a position of the distal end 62 of the catheter 61 at a time point T2 prior to the time point T1. The position P3 is a position of the distal end 62 of the catheter 61 at a time point T3 prior to the time point T2. The position P4 is a position of the distal end 62 of the catheter 61 at a time point T4 prior to the time point T3. The display 16 displays, as the position of the catheter 61 at the time point T1, the first figure 71 representing the series of positions P1, P2, P3, and P4.

In the example of FIG. 5, the current display mode is the second mode. The same position P1 is continuously detected from the data obtained in time series by the ultrasound transducer 25 for a certain period of time from the time point T1, and at a subsequent time point T1', a different position P1' is detected from the data obtained by the ultrasound transducer 25. The position P1' is a position of the distal end 62 of the catheter 61 at the time point T1' after a certain period of time elapsed from the time point T1. The position P1' and the position P1 are the same in positions in the Z-direction. That is, at the position P1' and the position P1, corresponding positions of the ultrasound transducer 25 are the same. The display 16 displays, as the position of the catheter 61 within a certain period of time from the time point T1, the second figure 72 representing one position P1 among the series of positions P1, P2, P3, and P4, and then displays, as the position of the catheter 61 at the time point T1', the second figure 72 representing one position P1' among the series of positions P1', P1, P2, P3, and P4.

A configuration of an image processing system 10 according to the present embodiment will be described with reference to FIG. 1.

The image processing system 10 can include the image processing device 11, a cable 12, a drive unit 13, a keyboard 14, a mouse 15, and the display 16.

The image processing device 11 can be a dedicated computer specialized for image diagnosis in the present embodiment, but may also be a general-purpose computer such as a personal computer (PC).

The cable 12 is used to connect the image processing device 11 and the drive unit 13.

Figure 2:
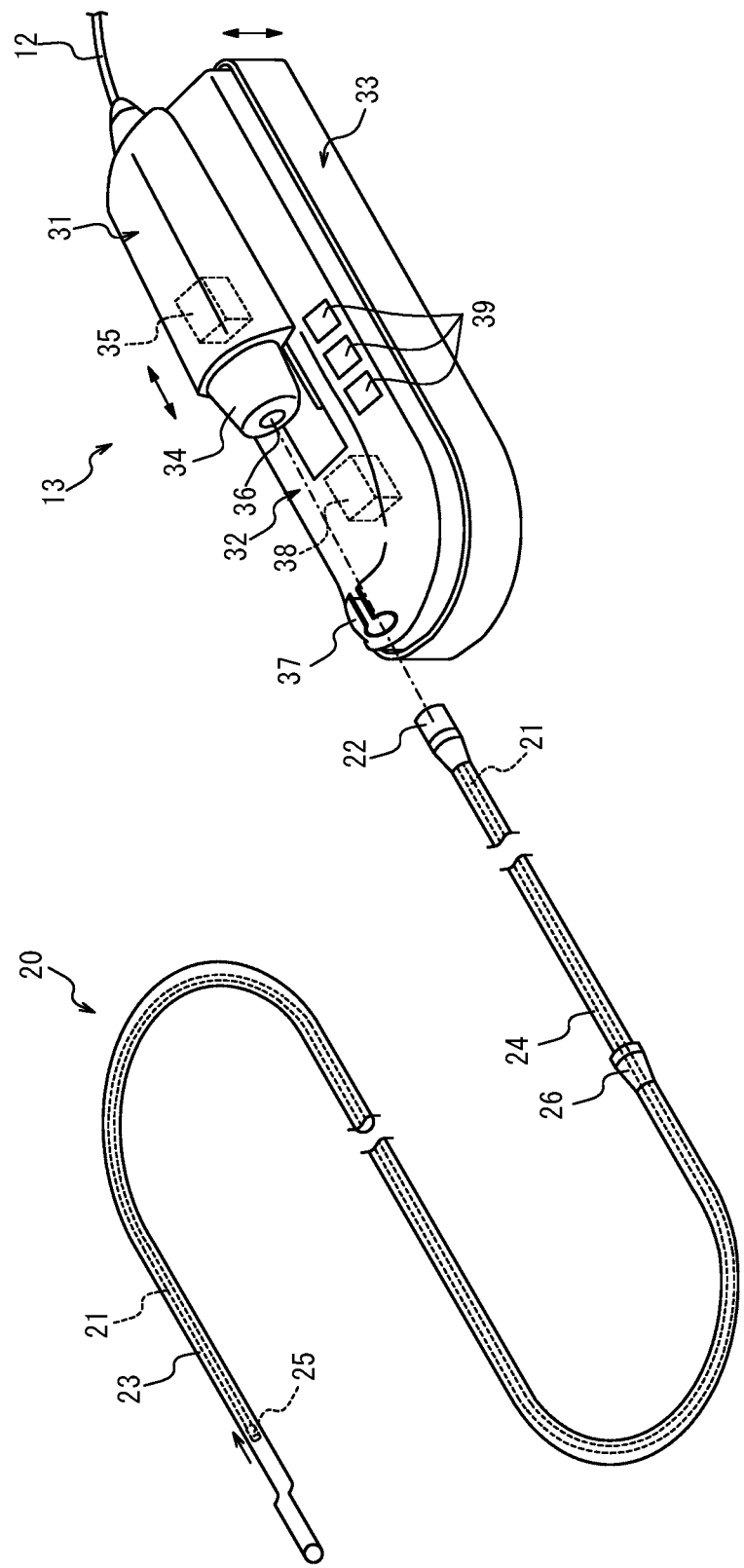
FIG. 2 is a perspective view of a probe and a drive unit of the image processing system according to the aspect of the present disclosure.

The drive unit 13 is a device to be used by connecting to a probe 20 illustrated in FIG. 2 to drive the probe 20. The drive unit 13 is also referred to as a motor drive unit (MDU). The probe 20 is applied to IVUS. The probe 20 is also referred to as an IVUS catheter or an image diagnostic catheter.

The keyboard 14, the mouse 15, and the display 16 are connected to the image processing device 11 via any cable or wirelessly. The display 16 can be, for example, a liquid crystal display (LCD), an organic electro luminescence (EL) display, or a head-mounted display (HMD).

The image processing system 10 optionally further includes a connection terminal 17 and a cart unit 18.

The connection terminal 17 is used to connect the image processing device 11 and an external device. The connection terminal 17 is, for example, a universal serial bus (USB) terminal. The external device can be, for example, a recording medium such as a magnetic disc drive, a magneto-optical disc drive, or an optical disc drive.

The cart unit 18 can be a cart equipped with casters for movement. The image processing device 11, the cable 12, and the drive unit 13 are disposed on a cart body of the cart unit 18. The keyboard 14, the mouse 15, and the display 16 are disposed on an uppermost table of the cart unit 18.

Configurations of the probe 20 and the drive unit 13 according to the present embodiment will be described with reference to FIG. 2.

The probe 20 can include a drive shaft 21, a hub 22, a sheath 23, an outer tube 24, the ultrasound transducer 25, and a relay connector 26.

The drive shaft 21 passes through the sheath 23 to be inserted into a body cavity of a living body and the outer tube 24 connected to a proximal end of the sheath 23, and extends to an inside of the hub 22 provided at a proximal end of the probe 20. The drive shaft 21 is provided with the ultrasound transducer 25, which transmits and receives signals, at a distal end of the drive shaft 21, and is rotatably provided in the sheath 23 and the outer tube 24. The relay connector 26 connects the sheath 23 and the outer tube 24.

The hub 22, the drive shaft 21, and the ultrasound transducer 25 are connected to each other to integrally move forward and backward in an axial direction. Therefore, for example, when the hub 22 is pressed toward a distal side, the drive shaft 21 and the ultrasound transducer 25 move inside the sheath 23 toward the distal side. For example, when the hub 22 is pulled toward a proximal side, the drive shaft 21 and the ultrasound transducer 25 move inside the sheath 23 toward the proximal side as indicated, for example, by an arrow in FIG. 2.

The drive unit 13 can include a scanner unit 31, a slide unit 32, and a bottom cover 33.

The scanner unit 31 is connected to the image processing device 11 via the cable 12. The scanner unit 31 can include a probe connection section 34 connected to the probe 20, and a scanner motor 35 which is a drive source for rotating the drive shaft 21.

The probe connection section 34 is freely detachably connected to the probe 20 through an insertion port 36 of the hub 22 provided at the proximal end of the probe 20. Inside the hub 22, a proximal end of the drive shaft 21 is rotatably supported, and a rotational force of the scanner motor 35 is transmitted to the drive shaft 21. A signal is transmitted and received between the drive shaft 21 and the image processing device 11 via the cable 12. In the image processing device 11, generation of a tomographic image of a body lumen and image processing is executed based on the signal transmitted from the drive shaft 21.

The slide unit 32 is mounted with the scanner unit 31 in a manner of being capable of moving forward and backward, and is mechanically and electrically connected to the scanner unit 31. The slide unit 32 can include a probe clamp section 37, a slide motor 38, and a switch group 39.

The probe clamp section 37 is disposed coaxially with the probe connection section 34 on the distal side relative to the probe connection section 34, and supports the probe 20 to be connected to the probe connection section 34.

The slide motor 38 is a drive source that generates a driving force in the axial direction. The scanner unit 31 moves forward and backward when driven by the slide motor 38, and the drive shaft 21 moves forward and backward in the axial direction accordingly. The slide motor 38 can be, for example, a servo motor.

The switch group 39 can include, for example, a forward switch and a pull-back switch that are pressed when the scanner unit 31 is to be moved forward or backward, and a scan switch that is pressed when image drawing is to be started or ended. Various switches may be included in the switch group 39 as necessary without being limited to the example here.

When the forward switch is pressed, the slide motor 38 rotates forward, and the scanner unit 31 moves forward. Meanwhile, when the pull-back switch is pressed, the slide motor 38 rotates backward, and the scanner unit 31 moves backward.

When the scan switch is pressed, the image drawing is started, the scanner motor 35 is driven, and the slide motor 38 is driven to move the scanner unit 31 backward. The user such as the operator connects the probe 20 to the scanner unit 31 in advance, such that the drive shaft 21 rotates and moves toward the proximal side in the axial direction upon the start of the image drawing. When the scan switch is pressed again, the scanner motor 35 and the slide motor 38 are stopped, and the image drawing is ended.

The bottom cover 33 covers a bottom and an entire circumference of a side surface on a bottom side of the slide unit 32, and is capable of moving toward and away from the bottom of the slide unit 32.

Figure 3:
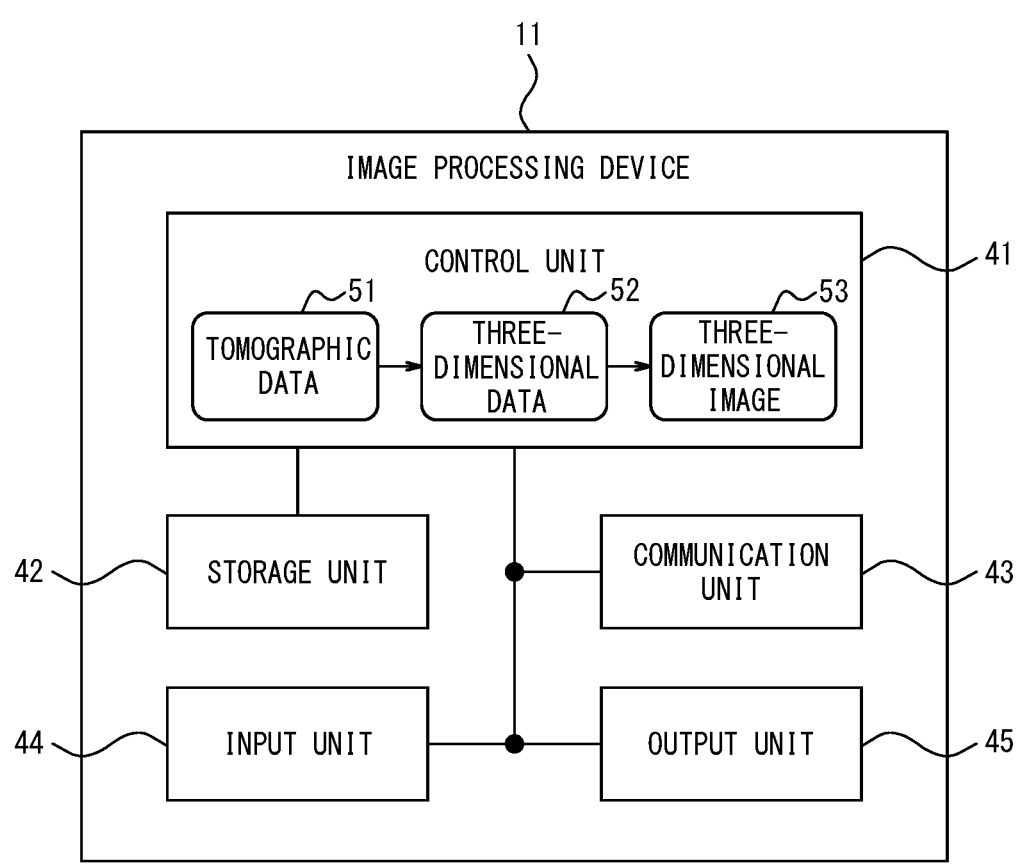
FIG. 3 is a block diagram illustrating a configuration of an image processing device according to the aspect of the present disclosure.

A configuration of the image processing device 11 will be described with reference to FIG. 3.

The image processing device 11 can include a control unit 41, a storage unit 42, a communication unit 43, an input unit 44, and an output unit 45.

The control unit 41 can include at least one processor, at least one dedicated circuit, or a combination of the least one processor and the at least one dedicated circuit. The processor is a general-purpose processor such as a central processing unit (CPU) or graphics processing unit (GPU), or a dedicated processor specialized for specific processing. The dedicated circuit can be, for example, a field-programmable gate array (FPGA) or an application specific integrated circuit (ASIC). The control unit 41 executes processing related to an operation of the image processing device 11 while controlling each unit of the image processing system 10 including the image processing device 11.

The storage unit 42 can include at least one semiconductor memory, at least one magnetic memory, at least one optical memory, or a combination of at least two of the at least one semiconductor, the at least one magnetic memory, and the at least one optical memory. The semiconductor memory can be, for example, a random-access memory (RAM) or a read only memory (ROM). The RAM can be, for example, a static random-access memory (SRAM) or a dynamic random access memory (DRAM). The ROM can be, for example, an electrically erasable programmable read only memory (EEPROM). The storage unit 42 can function as, for example, a main storage device, an auxiliary storage device, or a cache memory. The storage unit 42 stores data used for the operation of the image processing device 11, such as tomographic data 51, and data obtained by the operation of the image processing device 11, such as the three-dimensional data 52 and the three-dimensional image 53.

The communication unit 43 includes at least one communication interface. The communication interface can be, for example, a wired LAN interface, a wireless local area network (LAN) interface, or an image diagnostic interface for receiving IVUS signals and executing analog to digital (ND) conversion for the IVUS signals. The communication unit 43 receives the data used for the operation of the image processing device 11 and transmits the data obtained by the operation of the image processing device 11. In the present embodiment, the drive unit 13 is connected to the image diagnostic interface included in the communication unit 43.

The input unit 44 includes at least one input interface. The input interface can be, for example, a USB interface, a High-Definition Multimedia Interface (HDMI®) interface, or an interface compatible with short-range wireless communication such as Bluetooth®. The input unit 44 receives an operation of the user such as an operation of inputting the data used for the operation of the image processing device 11. In the present embodiment, the keyboard 14 and the mouse 15 are connected to the USB interface or the interface compatible with short-range wireless communication included in the input unit 44. When a touch screen is provided integrally with the display 16, the display 16 may be connected to the USB interface or the HDMI interface included in the input unit 44.

The output unit 45 includes at least one output interface. The output interface can be, for example, a USB interface, an HDMI interface, or an interface compatible with short-range wireless communication such as Bluetooth. The output unit 45 outputs the data obtained by the operation of the image processing device 11. In the present embodiment, the display 16 is connected to the USB interface or the HDMI interface included in the output unit 45.

A function of the image processing device 11 is implemented by executing an image processing program according to the present embodiment by the processor corresponding to the control unit 41. That is, the function of the image processing device 11 is implemented by software. The image processing program causes a computer to function as the image processing device 11 by causing the computer to execute processing of the image processing device 11. That is, the computer functions as the image processing device 11 by executing the processing of the image processing device 11 according to the image processing program.

The program may be stored in a non-transitory computer-readable medium in advance. The non-transitory computer-readable medium can be, for example, a flash memory, a magnetic recording device, an optical disc, a magneto-optical recording medium, or a ROM. Distribution of the program is executed by, for example, selling, transferring, or lending a portable medium such as a secure digital (SD) card, a digital versatile disc (DVD) or a compact disc read only memory (CD-ROM) storing the program. The program may be distributed by storing the program in a storage of a server in advance and transferring the program from the server to another computer. The program may be provided as a program product.

For example, the computer temporarily stores, in the main storage device, the program stored in the portable medium or the program transferred from the server. The computer reads, by the processor, the program stored in the main storage device, and executes, by the processor, processing according to the read program. The computer may read the program directly from the portable medium and execute the processing according to the program. Each time the program is transferred from the server to the computer, the computer may sequentially execute processing according to the received program. The processing may be executed by a so-called application service provider (ASP) type service in which the function is implemented only by execution instruction and result acquisition without transferring the program from the server to the computer. The program includes information provided for processing by an electronic computer and conforming to the program. For example, data that is not a direct command to the computer but has a property that defines the processing of the computer corresponds to the "information conforming to the program".

The functions of the image processing device 11 may be partially or entirely implemented by the dedicated circuit corresponding to the control unit 41. That is, the functions of the image processing device 11 may be partially or entirely implemented by hardware.

An operation of the image processing system 10 according to the present embodiment will be described with reference to FIGS. 6 to 11. The operation of the image processing system 10 corresponds to an image display method according to the present embodiment.

Figure 6:
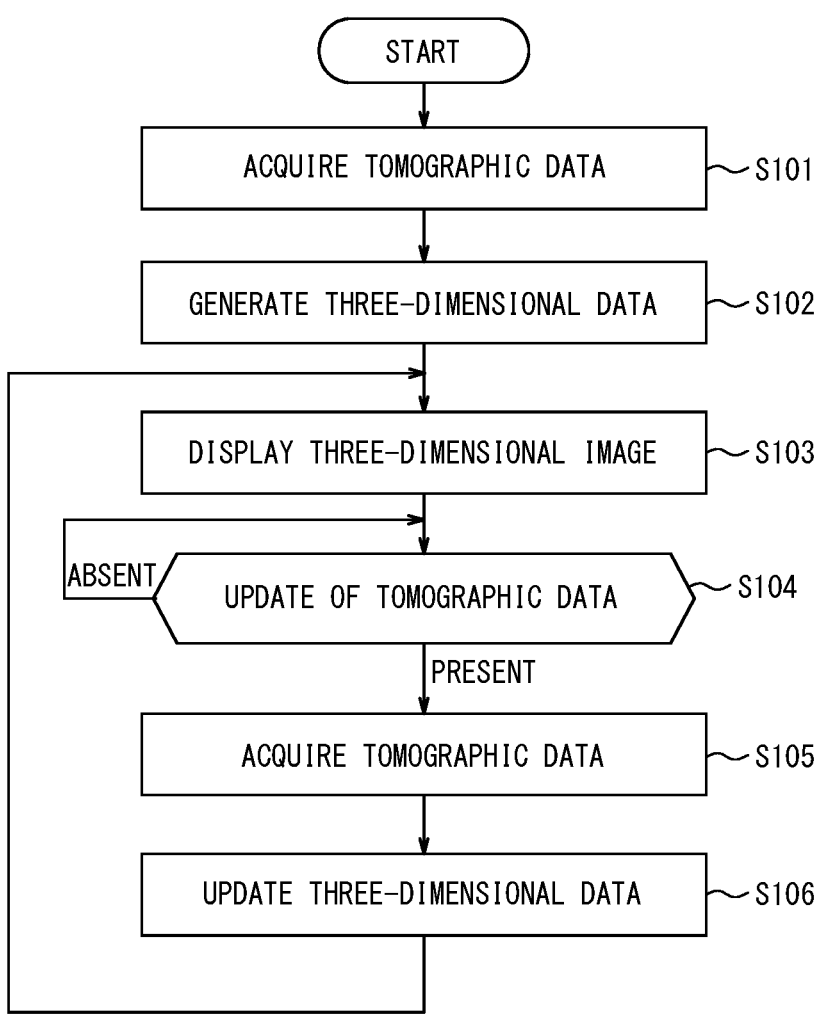
FIG. 6 is a flowchart illustrating an operation of the image processing system according to the aspect of the present disclosure.

Before a start of a flow in FIG. 6, the probe 20 is primed by the user. Thereafter, the probe 20 is fitted into the probe connection section 34 and the probe clamp section 37 of the drive unit 13, and is connected and fixed to the drive unit 13. Then, the probe 20 is inserted to a target site in the biological tissue 60 such as the blood vessel or the heart.

In S101, the scan switch included in the switch group 39 is pressed, and a so-called pull-back operation is executed by pressing the pull-back switch included in the switch group 39. The probe 20 transmits an ultrasound wave inside the biological tissue 60 by the ultrasound transducer 25 that moves backward in the axial direction by the pull-back operation. The ultrasound transducer 25 radially transmits the ultrasound wave while moving inside the biological tissue 60. The ultrasound transducer 25 receives a reflected wave of the transmitted ultrasound wave. The probe 20 inputs a signal of the reflected wave received by the ultrasound transducer 25 to the image processing device 11. The control unit 41 of the image processing device 11 processes the input signal to sequentially generate cross-sectional images of the biological tissue 60, thereby acquiring the tomographic data 51, which includes a plurality of cross-sectional images.

Specifically, the probe 20 transmits the ultrasound wave in a plurality of directions from a rotation center to an outside by the ultrasound transducer 25 while causing the ultrasound transducer 25 to rotate in a circumferential direction and to move in the axial direction inside the biological tissue 60. The probe 20 receives the reflected wave from a reflecting object present in each of the plurality of directions inside the biological tissue 60 by the ultrasound transducer 25. The probe 20 transmits the signal of the received reflected wave to the image processing device 11 via the drive unit 13 and the cable 12. The communication unit 43 of the image processing device 11 receives the signal transmitted from the probe 20. The communication unit 43 executes A/D conversion for the received signal. The communication unit 43 inputs the A/D-converted signal to the control unit 41. The control unit 41 processes the input signal to calculate an intensity value distribution of the reflected wave from the reflecting object present in a transmission direction of the ultrasound wave of the ultrasound transducer 25. The control unit 41 sequentially generates two-dimensional images having a luminance value distribution corresponding to the calculated intensity value distribution as the cross-sectional images of the biological tissue 60, thereby acquiring the tomographic data 51 which is a data set of the cross-sectional images. The control unit 41 stores the acquired tomographic data 51 in the storage unit 42.

In the present embodiment, the signal of the reflected wave received by the ultrasound transducer 25 corresponds to raw data of the tomographic data 51, and the cross-sectional images generated by processing the signal of the reflected wave by the image processing device 11 correspond to processed data of the tomographic data 51.

In a modification of the present embodiment, the control unit 41 of the image processing device 11 may store the signal input from the probe 20 as it is in the storage unit 42 as the tomographic data 51. Alternatively, the control unit 41 may store data indicating the intensity value distribution of the reflected wave calculated by processing the signal input from the probe 20 in the storage unit 42 as the tomographic data 51. That is, the tomographic data 51 is not limited to the data set of the cross-sectional images of the biological tissue 60, and may be data representing a cross section of the biological tissue 60 at each moving position of the ultrasound transducer 25 in any format.

In a modification of the present embodiment, an ultrasound transducer that transmits the ultrasound wave in the plurality of directions without rotating may be used instead of the ultrasound transducer 25 that transmits the ultrasound wave in the plurality of directions while rotating in the circumferential direction.

In a modification of the present embodiment, the tomographic data 51 may be acquired using optical frequency domain imaging (OFDI) or optical coherence tomography (OCT) instead of being acquired by using IVUS. When OFDI or OCT is used, as a sensor that acquires the tomographic data 51 while moving in the lumen of the biological tissue 60, a sensor that acquires the tomographic data 51 by emitting light in the lumen of the biological tissue 60 is used instead of the ultrasound transducer 25 that acquires the tomographic data 51 by transmitting the ultrasound wave in the lumen of the biological tissue 60.

In a modification of the present embodiment, instead of the image processing device 11 generating the data set of the cross-sectional images of the biological tissue 60, another device may generate the same data set, and the image processing device 11 may acquire the data set from the other device. That is, instead of the control unit 41 of the image processing device 11 processing the IVUS signal to generate the cross-sectional images of the biological tissue 60, another device may process the IVUS signal to generate the cross-sectional images of the biological tissue 60 and input the generated cross-sectional images to the image processing device 11.

In S102, the control unit 41 of the image processing device 11 generates the three-dimensional data 52 of the biological tissue 60 based on the tomographic data 51 acquired in S101.

Specifically, the control unit 41 of the image processing device 11 generates the three-dimensional data 52 of the biological tissue 60 by stacking the cross-sectional images of the biological tissue 60 included in the tomographic data 51 stored in the storage unit 42, and converting the same into three-dimensional data. As a method for three-dimensional conversion, any method among a rendering method such as surface rendering or volume rendering, and various processing such as texture mapping including environment mapping, and bump mapping, which is associated with the rendering method, is used. The control unit 41 stores the generated three-dimensional data 52 in the storage unit 42.

In S103, the control unit 41 of the image processing device 11 causes the display 16 to display the three-dimensional data 52 generated in S102 as the three-dimensional image 53.

Specifically, the control unit 41 of the image processing device 11 generates the three-dimensional image 53 based on the three-dimensional data 52 stored in the storage unit 42. The control unit 41 causes the display 16 to display the generated three-dimensional image 53 via the output unit 45.

In S104, if the tomographic data 51 is updated, processing of S105 and S106 is executed.

In S105, similarly to the processing of S101, the control unit 41 of the image processing device 11 processes the signal input from the probe 20 to newly generate cross-sectional images of the biological tissue 60, thereby acquiring the tomographic data 51 including at least one new cross-sectional image.

In S106, the control unit 41 of the image processing device 11 updates the three-dimensional data 52 of the biological tissue 60 based on the tomographic data 51 acquired in S105. Then, in S103, the control unit 41 causes the display 16 to display the three-dimensional data 52 updated in S106 as the three-dimensional image 53.

In a modification of the present embodiment, as a user operation, the control unit 41 of the image processing device 11 may receive, via the input unit 44, an operation of setting an angle for displaying the three-dimensional image 53. In this case, the control unit 41 adjusts the angle for displaying the three-dimensional image 53 to the set angle. Then, the control unit 41 causes the display 16 to display the three-dimensional image 53 at the set angle.

In a modification of the present embodiment, as a user operation, the control unit 41 of the image processing device 11 may receive, via the input unit 44, an operation of setting an opening for exposing the lumen of the biological tissue 60 in the three-dimensional image 53. In this case, the control unit 41 forms the set opening in the three-dimensional data 52. The control unit 41 causes the display 16 to display the three-dimensional data 52 as the three-dimensional image 53, and adjusts a viewpoint when displaying the three-dimensional image 53 on the display 16 according to a position of the opening formed in the three-dimensional data 52. The term "viewpoint" refers to a position of a virtual camera disposed in a three-dimensional space. For example, the control unit 41 arranges the viewpoint on a straight line extending from an inner surface of the biological tissue 60 to an outside of the biological tissue 60 through the opening. Accordingly, the user can virtually observe the inner surface of the biological tissue 60 by looking into the biological tissue 60 through the opening.

Figure 7:
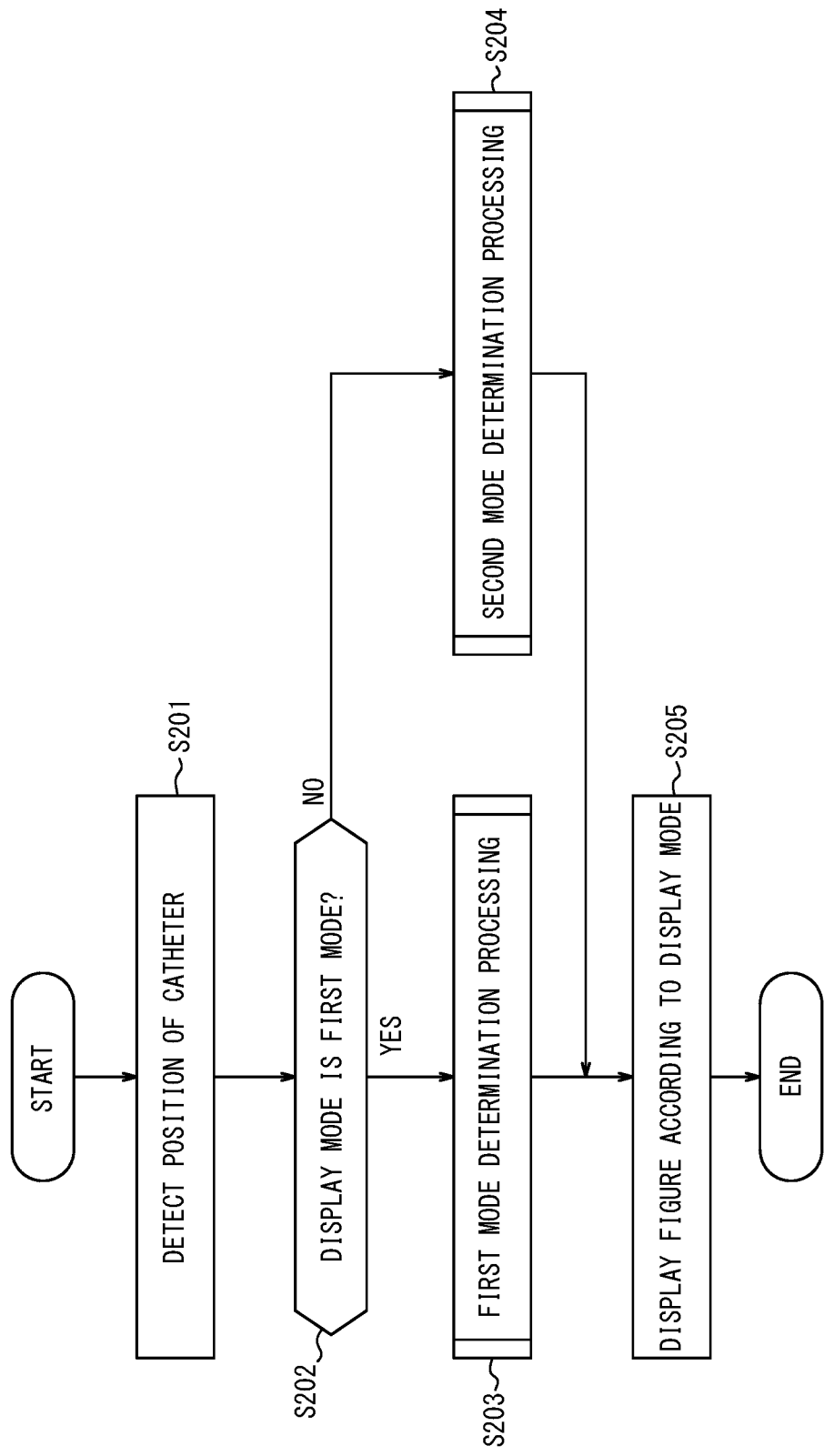
FIG. 7 is a flowchart illustrating an operation of the image processing system according to the aspect of the present disclosure.

A flow of FIG. 7 is started when the position of the catheter 61 inserted into the biological tissue 60 is to be displayed in the three-dimensional image 53 in S103. Whether to display the position of the catheter 61 may be automatically determined depending on the presence or absence of the catheter 61, or may be manually determined according to the user operation.

In S103 subsequent to S102, processing of S201 to S205 is executed for each of the plurality of cross-sectional images included in the tomographic data 51 acquired in S101. In S103 subsequent to S106, the processing of S201 to S205 is executed for the new cross-sectional image included in the tomographic data 51 acquired in S105.

Hereinafter, a procedure in which the processing of S201 to S205 is executed for a cross-sectional image obtained at a certain time point Ti will be described.

In S201, the control unit 41 of the image processing device 11 detects, by using any method such as machine learning, a position Pi of the catheter 61 from the cross-sectional image obtained at the time point Ti.

In S202, if the current display mode is the first mode, first mode determination processing of S203 is executed. If the current display mode is the second mode, second mode determination processing of S204 is executed.

Figure 8:
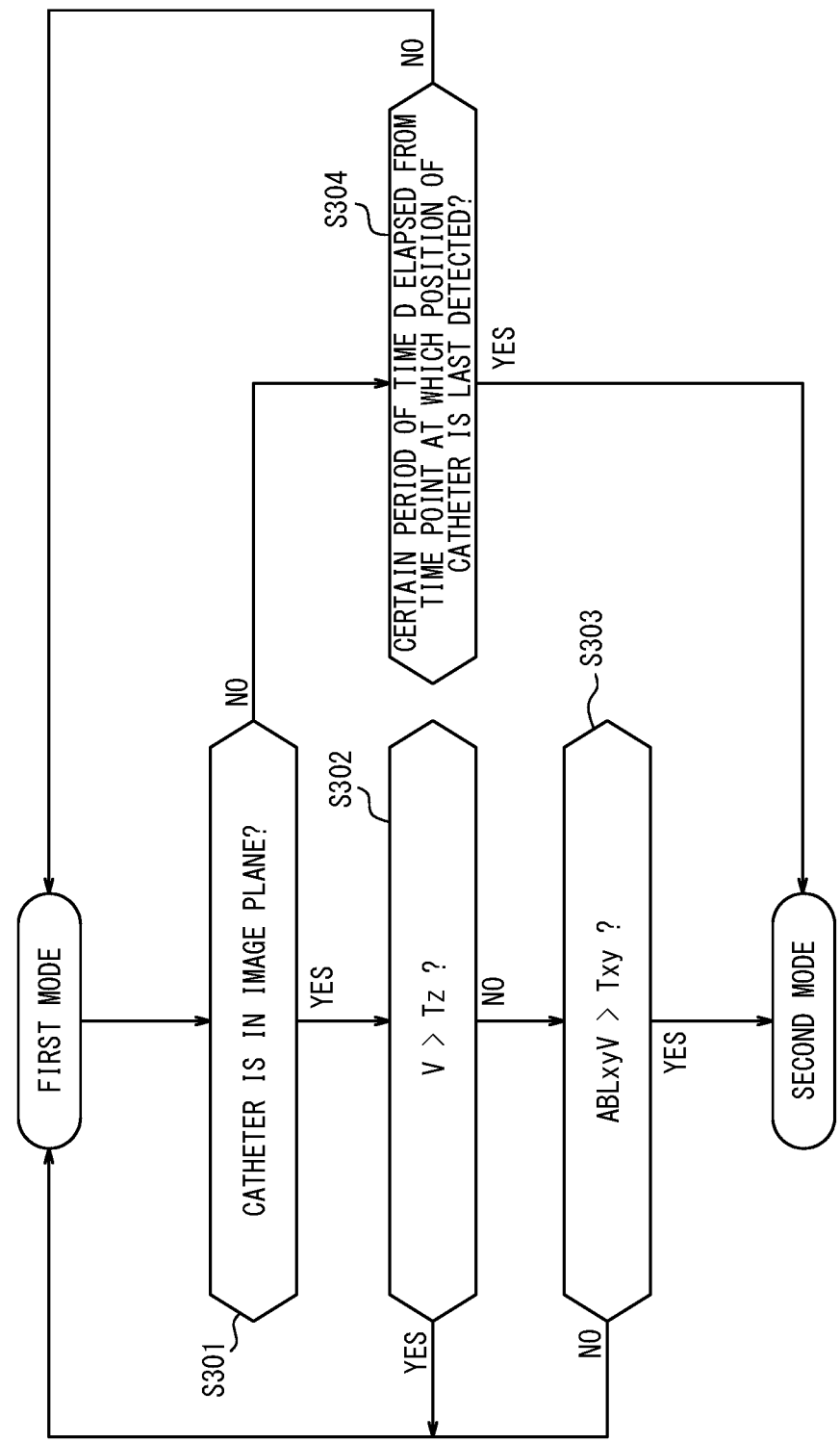
FIG. 8 is a flowchart illustrating a procedure of first mode determination processing of FIG. 7.

A procedure of the first mode determination processing of S203 is illustrated in FIG. 8.

Figure 9:
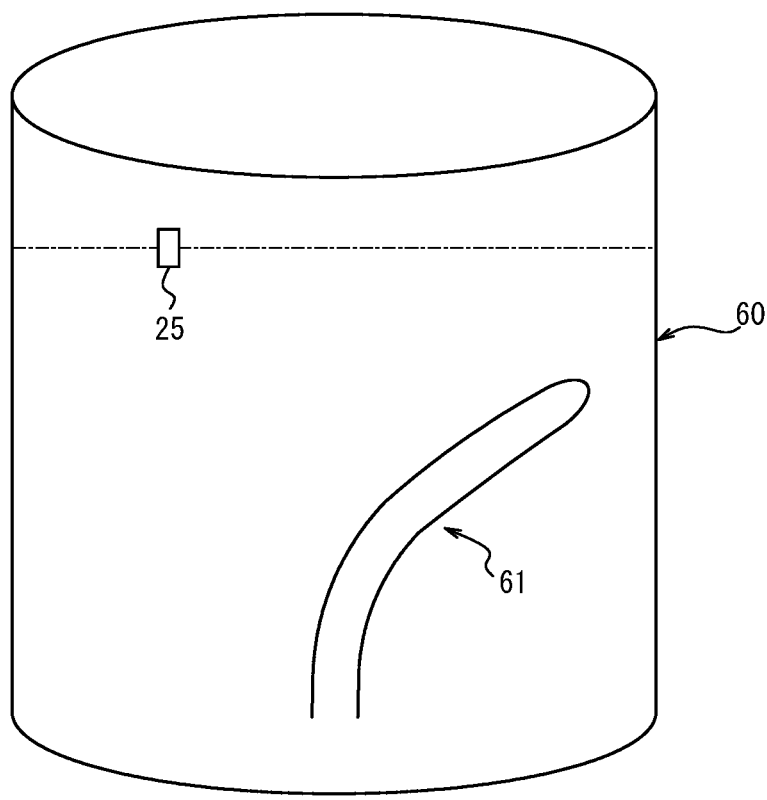
FIG. 9 is a diagram illustrating an example in which a catheter is not present in an image plane.

In S301, the control unit 41 of the image processing device 11 determines whether the catheter 61 is present in an image plane captured by the ultrasound transducer 25 at the time point Ti. If the position Pi of the catheter 61 is detected in S201, the catheter 61 is present in the image plane captured by the ultrasound transducer 25, and thus processing of S302 is executed. If the position Pi of the catheter 61 is not detected in S201, as illustrated in FIG. 9, the catheter 61 is not present in the image plane captured by the ultrasound transducer 25, and thus processing of S304 is executed.

In S302, the control unit 41 of the image processing device 11 determines whether a moving speed V of the ultrasound transducer 25 at the time point Ti exceeds a threshold value Tz. If the moving speed V does not exceed the threshold value Tz, processing of S303 is executed. If the moving speed V exceeds the threshold value Tz, the display mode is not switched, and the processing of S205 is executed in the first mode.

The moving speed V of the ultrasound transducer 25 is a distance by which the ultrasound transducer 25 moves per unit time along the axial direction of the catheter 61, that is, a traveling direction of the lumen of the biological tissue 60, rather than a rotation direction of the ultrasound transducer 25.

The threshold value Tz may be a value as low as possible such that stop of a movement of the ultrasound transducer 25 can be detected, and is 0 in the present embodiment. The threshold value Tz may be set to a value of 0.01 mm/frames per second (mm/FPS) or more and 1 cm/FPS or less. FPS refers to the number of cross-sectional images updated per second.

In S303, the control unit 41 of the image processing device 11 determines whether a magnitude ABLxyV of the movement of the catheter 61 per unit time in the image plane captured by the ultrasound transducer 25 at the time point Ti exceeds a threshold value Txy. If the magnitude ABLxyV does not exceed the threshold value Txy, the display mode is not switched, and the processing of S205 is executed in the first mode. If the magnitude ABLxyV exceeds the threshold value Txy, the control unit 41 switches the display mode from the first mode to the second mode. Thereafter, the processing of S205 is executed. For example, when the operator executes ablation, the ablation catheter is moved on the same plane and the inner surface of the biological tissue 60 is cauterized in a ring shape, and thus it is useful to switch the display mode to the second mode. Meanwhile, if there is no movement of the ablation catheter on the same plane, it is not necessary to switch the display mode to the second mode.

In S304, the control unit 41 of the image processing device 11 determines whether an elapsed time from a time point at which the position of the catheter 61 is last detected is equal to or greater than a threshold value D. If the elapsed time is less than the threshold value D, the display mode is not switched, and the processing of S205 is executed in the first mode. If the elapsed time is equal to or greater than the threshold value D, the control unit 41 switches the display mode from the first mode to the second mode. Thereafter, the processing of S205 is executed.

The threshold value D may be any value, and in the present embodiment, threshold value D is set to a value of 0 seconds or more and 10 seconds or less.

As described above, in the present embodiment, the control unit 41 of the image processing device 11 switches the display mode according to a change in a moving state of the ultrasound transducer 25. The change in the moving state of the ultrasound transducer 25 can include a case in which the moving speed V of the ultrasound transducer 25 exceeds the threshold value Tz. The control unit 41 switches the display mode according to whether the catheter 61 is present in the image plane captured by the ultrasound transducer 25.

Specifically, when the catheter 61 is present in the image plane captured by the ultrasound transducer 25, the control unit 41 switches the display mode according to a magnitude of the movement of the catheter 61 in the image plane. More specifically, the control unit 41 switches the display mode from the first mode to the second mode when the catheter 61 is present in the image plane captured by the ultrasound transducer 25, the moving speed V of the ultrasound transducer 25 does not exceed the threshold value Tz, and the magnitude ABLxyV of the movement of the catheter 61 per unit time in the image plane exceeds the threshold value Txy.

When the catheter 61 is not present in the image plane captured by the ultrasound transducer 25, the control unit 41 switches the display mode according to the elapsed time from the time point at which a last position among the detected series of positions of the catheter 61 is detected. More specifically, the control unit 41 switches the display mode from the first mode to the second mode when the catheter 61 is not present in the image plane captured by the ultrasound transducer 25, and the elapsed time from a last confirmation of the catheter 61 becomes equal to or greater than the threshold value D.

In a modification of the present embodiment, the control unit 41 may switch the display mode from the first mode to the second mode simply when the moving speed V of the ultrasound transducer 25 does not exceed the threshold value Tz. That is, the processing of S301, S303, and S304 may be omitted.

In a modification of the present embodiment, the control unit 41 may switch the display mode from the first mode to the second mode simply when the catheter 61 is present in the image plane captured by the ultrasound transducer 25, and the moving speed V of the ultrasound transducer 25 does not exceed the threshold value Tz. That is, the processing of S303 may be omitted.

Figure 10:
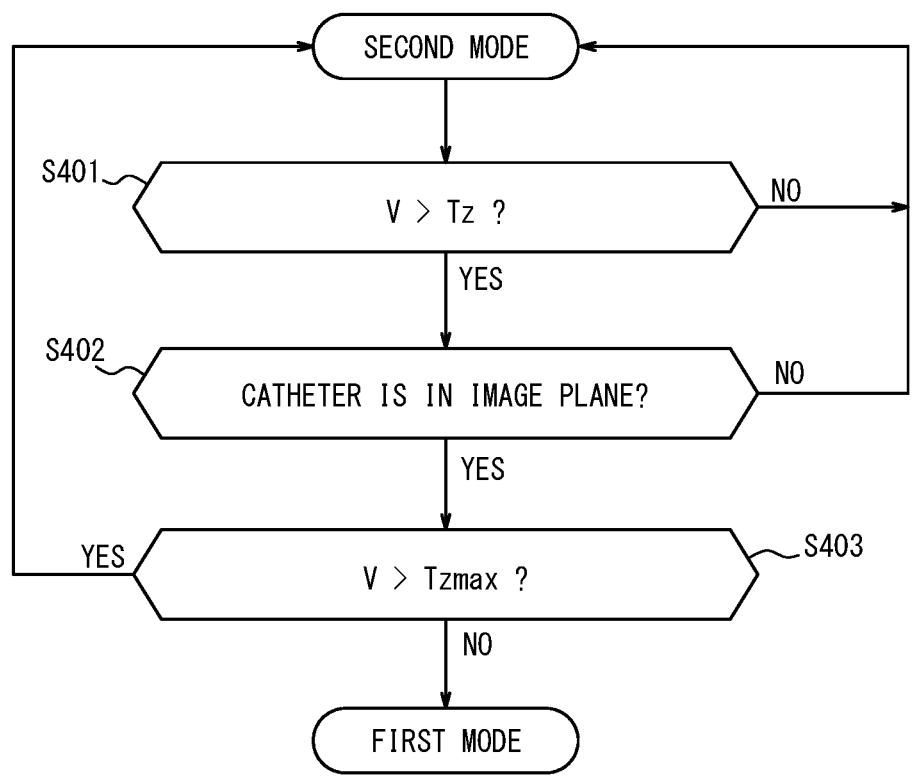
FIG. 10 is a flowchart illustrating a procedure of second mode determination processing of FIG. 7.

A procedure of the second mode determination processing of S204 is illustrated in FIG. 10.

In S401, the control unit 41 of the image processing device 11 determines whether the moving speed V of the ultrasound transducer 25 at the time point Ti exceeds the threshold value Tz. If the moving speed V exceeds the threshold value Tz, processing of S402 is executed. If the moving speed V does not exceed the threshold value Tz, the display mode is not switched, and the processing of S205 is executed in the second mode.

In S402, the control unit 41 of the image processing device 11 determines whether the catheter 61 is present in the image plane captured by the ultrasound transducer 25 at the time point Ti. If the position Pi of the catheter 61 is detected in S201, the catheter 61 is present in the image plane captured by the ultrasound transducer 25, and thus processing of S403 is executed. If the position Pi of the catheter 61 is not detected in S201, as illustrated in FIG. 9, the catheter 61 is not present in the image plane captured by the ultrasound transducer 25, and thus the display mode is not switched, and the processing of S205 is executed in the second mode.

Figure 11:
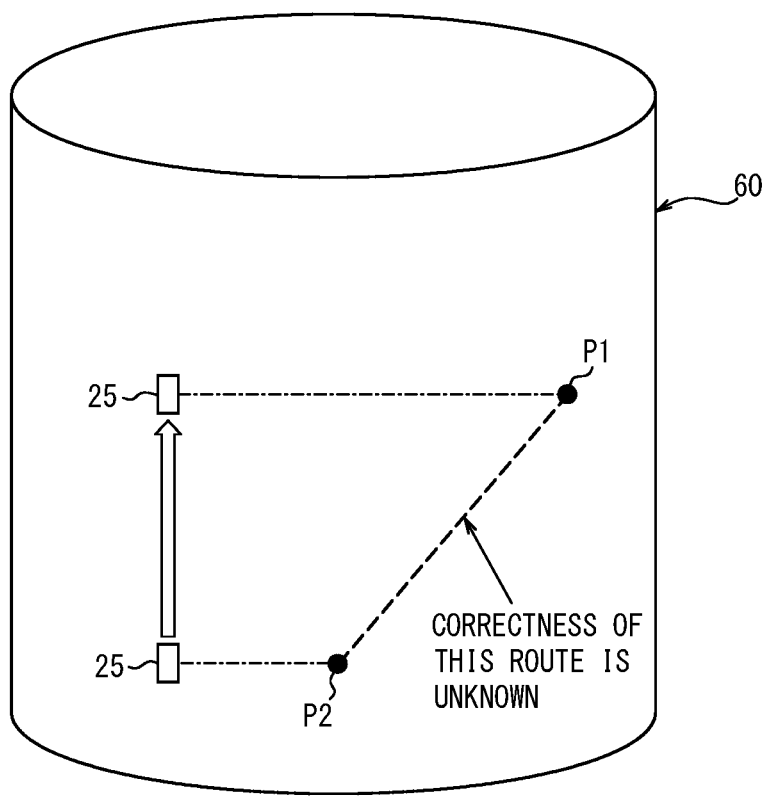
FIG. 11 is a diagram illustrating an example in which a moving speed of a sensor is too high.

In S403, the control unit 41 of the image processing device 11 determines whether the moving speed V of the ultrasound transducer 25 at the time point Ti exceeds an upper limit value Tzmax. If the moving speed V exceeds the upper limit value Tzmax, the display mode is not switched, and the processing of S205 is executed in the second mode. If the moving speed V does not exceed the upper limit value Tzmax, the control unit 41 switches the display mode from the second mode to the first mode. Thereafter, the processing of S205 is executed. For example, as illustrated in FIG. 11, if the moving speed V of the ultrasound transducer 25 is too high, there is a possibility that a correct trajectory of the catheter 61 cannot be obtained even when the prior position P2 and the current position P1 of the catheter 61 are directly connected to each other. In such a case, if the display mode remains in the second mode, the operator is prompted to move the ultrasound transducer 25 to execute scanning again.

As described above, in the present embodiment, the control unit 41 of the image processing device 11 switches the display mode according to the change in the moving state of the ultrasound transducer 25. The change in the moving state of the ultrasound transducer 25 includes the case in which the moving speed V of the ultrasound transducer 25 exceeds the threshold value Tz. The control unit 41 switches the display mode according to whether the catheter 61 is present in the image plane captured by the ultrasound transducer 25.

Specifically, when the moving speed V of the ultrasound transducer 25 exceeds the threshold value Tz, the control unit 41 switches the display mode according to whether the moving speed V of the ultrasound transducer 25 is equal to or less than the upper limit value Tzmax. More specifically, the control unit 41 switches the display mode from the second mode to the first mode when the moving speed V of the ultrasound transducer 25 exceeds the threshold value Tz, the catheter 61 is present in the image plane captured by the ultrasound transducer 25, and the moving speed V of the ultrasound transducer 25 is equal to or less than the upper limit value Tzmax, which is a maximum value allowed for the ultrasound transducer 25.

In a modification of the present embodiment, the control unit 41 may switch the display mode from the second mode to the first mode simply when the moving speed V of the ultrasound transducer 25 exceeds the threshold value Tz. That is, the processing of S402 and S403 may be omitted.

In a modification of the present embodiment, the control unit 41 may switch the display mode from the second mode to the first mode simply when the moving speed V of the ultrasound transducer 25 exceeds the threshold value Tz, and the catheter 61 is present in the image plane captured by the ultrasound transducer 25. That is, the processing of S403 may be omitted.

In S205, if the current display mode is the first mode, as in the example of FIG. 4, the control unit 41 of the image processing device 11 displays in the three-dimensional image 53 the first figure 71 representing the series of positions of the catheter 61 including the position Pi detected in S201 as a latest position. In the example of FIG. 4, if the time point T1 corresponds to the time point Ti, the position P1 corresponds to the position Pi.

In the example of FIG. 4, the first mode is a mode in which the past catheter positions are connected to display the catheter 61 like a tube, but in another example, the first mode may be a mode in which the catheter 61 is displayed like a single line. That is, the control unit 41 of the image processing device 11 may display, as the first figure 71, a linear figure connecting the series of positions of the catheter 61, instead of displaying a tubular figure connecting the series of positions of the catheter 61.

In S205, if the current display mode is the second mode, as in the example of FIG. 5, the control unit 41 of the image processing device 11 displays in the three-dimensional image 53 the second figure 72 representing the position Pi detected in S201 as the latest position. In the example of FIG. 5, if the time point T1 corresponds to the time point Ti, the position P1 corresponds to the position Pi. If the time point T1' corresponds to the time point Ti, the position P1' corresponds to the position Pi.

Figure 12:
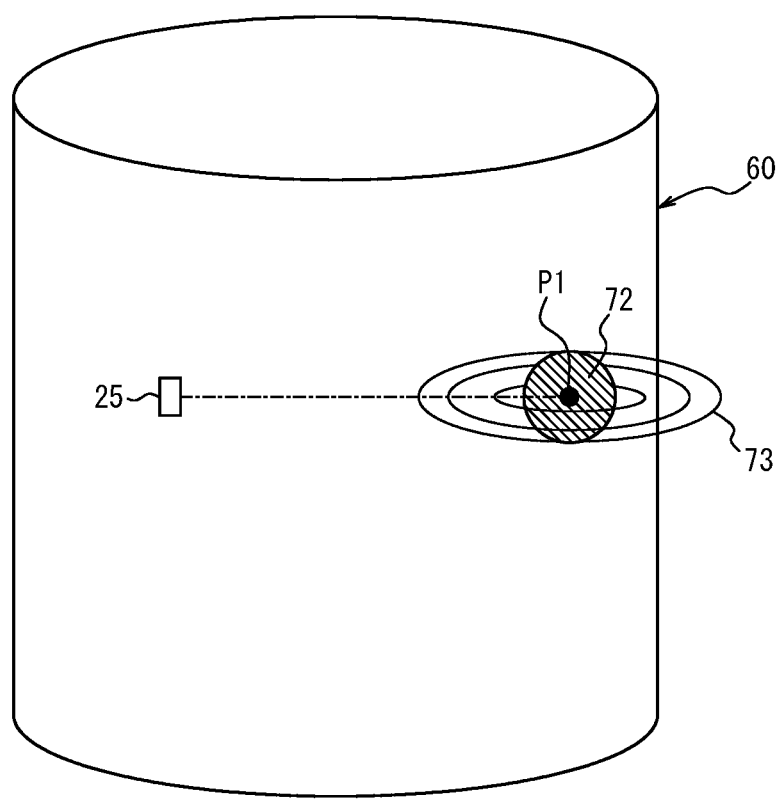
FIG. 12 is a diagram illustrating a three-dimensional image and a second figure displayed in a modification.

In the example of FIG. 5, the second mode is a mode in which the current catheter position is displayed like a sphere, but as in the example of FIG. 12, the second mode may be a mode in which the current catheter position is displayed like Saturn. That is, the control unit 41 of the image processing device 11 may display, as the second figure 72, a spherical figure representing one position of the series of positions of the catheter 61, and may display at least one concentric circle 73 surrounding the spherical figure. Alternatively, the control unit 41 may display, as the second figure 72, a spherical figure representing one position of the series of positions of the catheter 61, and may display at least one concentric sphere surrounding the spherical figure. When the concentric circle 73 or the concentric sphere is present, a distance to a blood vessel wall in the second mode is relatively easy to understand. In the example of FIG. 12, three concentric circles 73 are displayed, but the number of concentric circles 73 may be less than three or more than three.

In another example in which the distance to the blood vessel wall is relatively easy to understand in the second mode, a size of the second figure 72 may be changed according to the distance from the blood vessel wall, or a color of the second figure 72 may be changed according to the distance from the blood vessel wall. Alternatively, the second figure 72 may be shaded in the second mode. That is, in the second mode, the control unit 41 of the image processing device 11 may adjust at least one of the size or color of the second figure 72 according to the distance from an inner wall surface 63 of the biological tissue 60. Alternatively, the control unit 41 may further display the shadow of the second figure 72 in the second mode.

Figure 13:
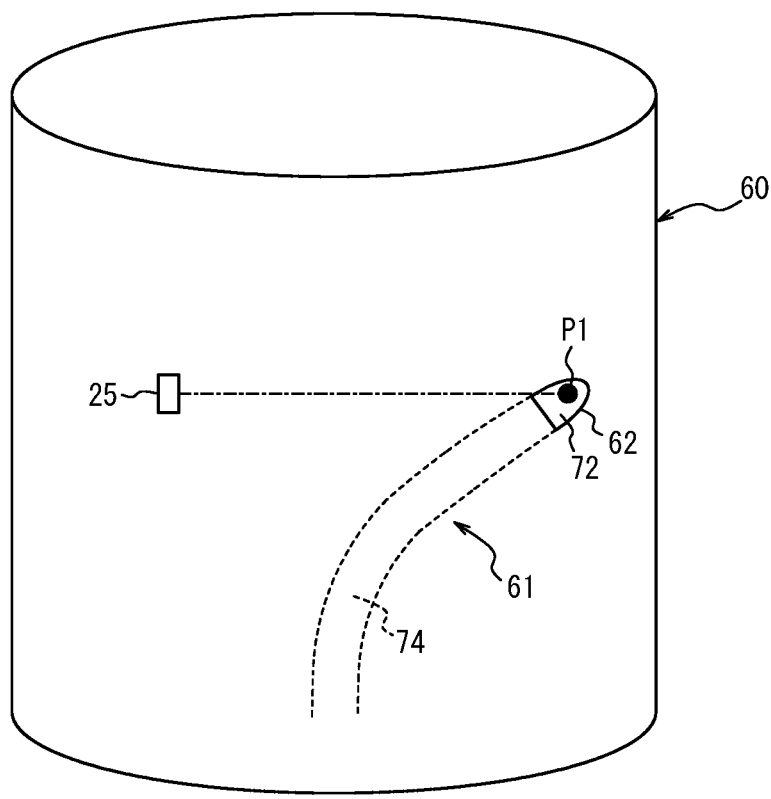
FIG. 13 is a diagram illustrating a three-dimensional image and a second figure displayed in a modification.

As in the example of FIG. 13, the second mode may be a mode in which the current catheter position is displayed like a bullet. That is, the control unit 41 of the image processing device 11 may display, as the second figure 72, a figure in which a thickness dimension on a side near an end of the catheter 61 is larger than a thickness dimension on an opposite side. Specifically, the control unit 41 may display, as the second figure 72, a bullet-shaped figure representing one position of the series of positions of the catheter 61. In particular, the control unit 41 may display, as the second figure 72, a bullet-shaped figure representing the position of the distal end 62 of the catheter 61. By illustrating the distal end 62 of the catheter 61 in a bullet shape, it is relatively easy to understand a moving direction of the catheter 61, such as whether the catheter 61 came from above or below.

Figure 14:
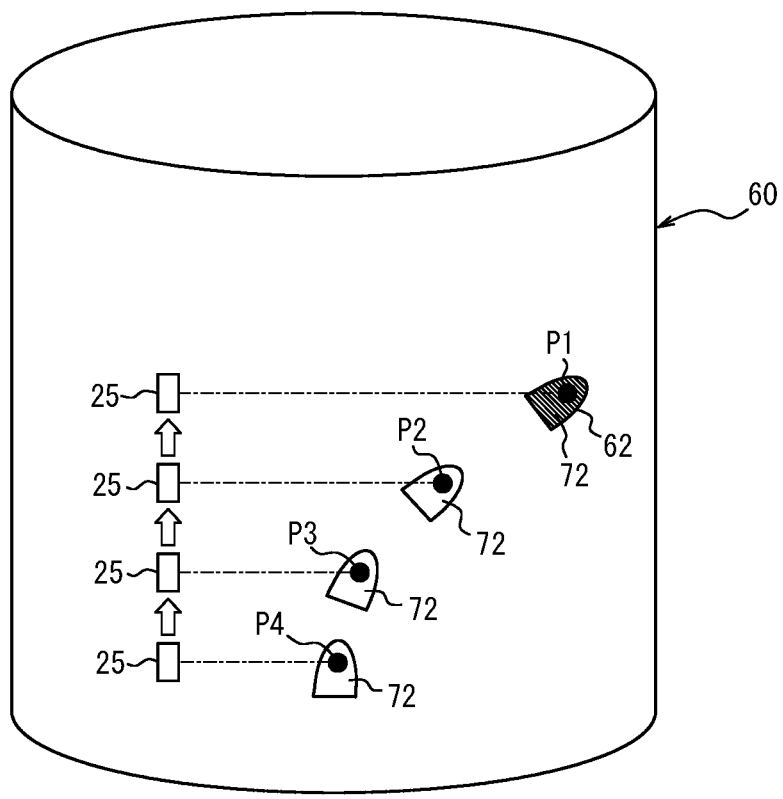
FIG. 14 is a diagram illustrating a three-dimensional image and a second figure displayed in a modification.

In the example of FIG. 5, the current catheter position is the position of the distal end 62 of the catheter 61, but the current catheter position may not be the position of the distal end 62 of the catheter 61. Therefore, as in the example of FIG. 14, if the current catheter position is not the position of the distal end 62 of the catheter 61, the color may be changed. That is, when displaying a figure representing a position other than the distal end 62 of the catheter 61 as the second figure 72, the control unit 41 of the image processing device 11 may display the second figure 72 in a color different from that when displaying the figure representing the position of the distal end 62 of the catheter 61 as the second figure 72.

Figure 15:
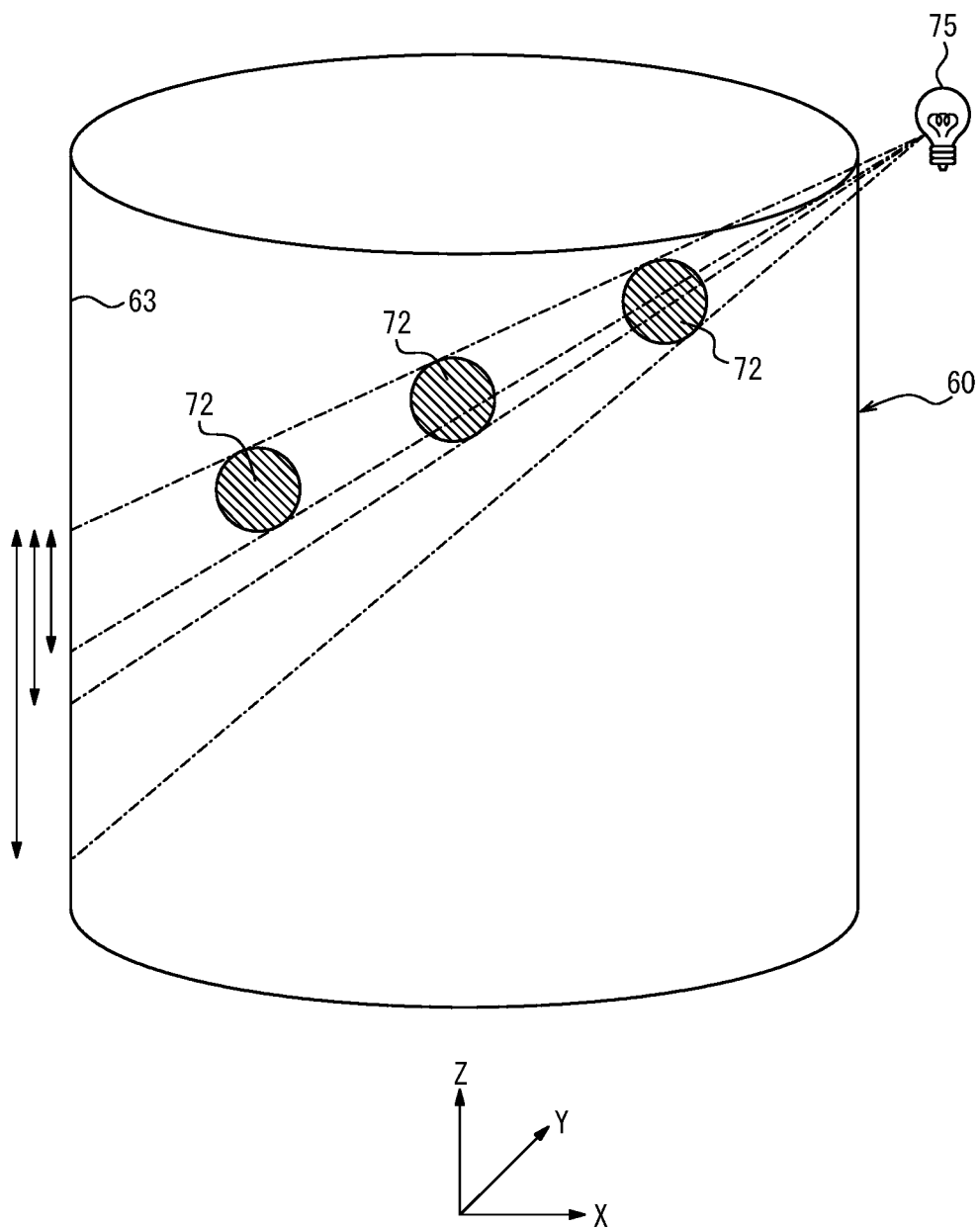
FIG. 15 is a diagram illustrating a three-dimensional image and a second figure displayed in a modification.

When the shadow of the second figure 72 is added in the second mode, as illustrated in FIG. 15, the shadow becomes smaller as the second figure 72 is closer to the blood vessel wall on a side farther from a virtual light source 75. Accordingly, it is preferable to express the catheter position in a relatively large size when the distance from the tissue is relatively long, and to express the catheter position in a relatively small size when the distance from the tissue is relatively short.

When changing the display mode from the first mode to the second mode, the second figure 72 can be easily seen if made relatively larger than a corresponding portion thereof in the first figure 71.

In an example in which it is easy to understand whether the catheter 61 is in contact with the tissue, if the catheter 61 is in contact with the blood vessel wall, the size of the second figure 72 may be changed, or the color of the second figure 72 may be changed. That is, in the second mode, the control unit 41 of the image processing device 11 may adjust at least one of the size or color of the second figure 72 according to the presence or absence of the contact with the inner wall surface 63 of the biological tissue 60.

In the present embodiment, the control unit 41 of the image processing device 11 switches the display mode according to the change in the moving state of the ultrasound transducer 25, but in a modification of the present embodiment, the control unit 41 may switch the display mode according to a change in a positional relation between the ultrasound transducer 25 and the catheter 61.

In the present embodiment, the control unit 41 of the image processing device 11 determines in time series whether the moving speed V of the ultrasound transducer 25 exceeds the threshold value Tz. When the moving speed V of the ultrasound transducer 25 does not exceed the threshold value Tz, and other requirements are also satisfied, the control unit 41 switches the display mode from the first mode to the second mode. That is, the control unit 41 represents the catheter 61 with one latest position instead of a series of positions when the ultrasound transducer 25 remains at the same position. Note that "other requirements" may not be imposed.

In the modification in which the display mode is switched according to the change in the positional relation between the ultrasound transducer 25 and the catheter 61, the control unit 41 determines in time series whether the magnitude ABLxyV of movement of the catheter 61 per unit time in the image plane captured by the ultrasound transducer 25 exceeds the threshold value Txy. When the magnitude ABLxyV of movement of the catheter 61 exceeds the threshold value Txy, and other requirements are also satisfied, the control unit 41 switches the display mode from the first mode to the second mode. That is, the control unit 41 represents the catheter 61 with one latest position instead of a series of positions when the catheter 61 is moving significantly in the Z-direction. Note that "other requirements" may not be imposed.

As described above, in the present embodiment, the control unit 41 of the image processing device 11 causes the display 16 to display the three-dimensional data 52 as the three-dimensional image 53, the three-dimensional data 52 representing the biological tissue 60. The control unit 41 detects the series of positions of the catheter 61 inserted into the biological tissue 60 from the tomographic data 51 obtained in time series by the ultrasound transducer 25 observing the surrounding of the lumen of the biological tissue 60 while moving in the lumen. The control unit 41 switches the display mode between the first mode for displaying the first figure 71 representing the series of positions in the three-dimensional image 53, and the second mode for displaying the second figure 72 representing one position among the series of positions in the three-dimensional image 53.

According to the present embodiment, it is possible to facilitate understanding of the position of the catheter 61 when displaying the catheter 61 in the three-dimensional image 53 of the biological tissue 60.

In the present embodiment, the control unit 41 of the image processing device 11 confirms the moving state of the pull-back unit one by one. When a movement of the pull-back unit stops, the control unit 41 displays the position of the catheter 61 by a display method such as a "point" indicating only the current position. When the pull-back unit starts to move again, the control unit 41 displays a travel history of the catheter 61 by a display method such as a "line" indicating a series of positions. When the pull-back unit returns to an original path again, the control unit 41 temporarily resets the display of the travel history, and displays the travel history from that time point.

According to the present embodiment, if the user is an operator, the user can execute treatment without being confused by the past information that does not have relevance to the current position of the catheter 61 when the movement of the pull-back unit stops.

In the present embodiment, when the tomographic data 51 including at least one new cross-sectional image is acquired, the processing of S201 to S205 is executed for the new cross-sectional image. That is, the first mode determination processing of S203 or the second mode determination processing of S204 is executed each time the tomographic data 51 is updated in S105. In S205, if the current display mode is the first mode, as in the example of FIG. 4, the first figure 71, which represents the series of positions of the catheter 61 and includes the position Pi detected in S201 as the latest position, is displayed in the three-dimensional image 53. This means that when the display mode is not switched, and the processing of S205 is executed in the first mode as a result of the first mode determination processing associated with the update of the tomographic data 51, the first figure 71 is updated. Meanwhile, in S205, if the current display mode is the second mode, as in the example of FIG. 5, the second figure 72 representing the position Pi detected in S201 as the latest position is displayed in the three-dimensional image 53, which means that when the display mode is not switched, and the processing of S205 is executed in the second mode as a result of the second mode determination processing associated with the update of the tomographic data 51, the second figure 72 is updated.

Even if the first figure 71 such as the "line" is frequently updated in the first mode, the first figure 71 is less noticeable to the user, but if the second figure 72 such as the "point" is frequently updated in the second mode, the updated second figure 72 appears as flickering, and may cause the user to feel uncomfortable or tired. If the user is an operator, a concentration may be reduced, which may adversely affect the treatment. Therefore, in a modification of the present embodiment, an update speed of the second figure 72 may be intentionally slowed down in the second mode. That is, in the second mode, the control unit 41 of the image processing device 11 may adjust an update frequency of the second figure 72 associated with the update of the tomographic data 51. For example, the control unit 41 may adjust the update speed of the second figure 72 to be lower by a fixed ratio or a variable ratio with respect to an update speed of the tomographic data 51. Alternatively, the control unit 41 may control the number of times of the update of the second figure 72 to be smaller than that of the tomographic data 51. In the first mode, the control unit 41 may update the first figure 71 each time the tomographic data 51 is updated, or may adjust an update frequency of the first figure 71 associated with the update of the tomographic data 51.

This modification will be further described.

In the second mode, the control unit 41 of the image processing device 11 intentionally causes a frame rate delay only for the catheter 61. For example, when the three-dimensional image 53 is updated at 30 FPS, vibration is intense in the display in the second mode, which may cause a phenomenon that the display is difficult to see. Therefore, the control unit 41 intentionally executes control to display the catheter position while reducing only the frame rate of the catheter position. Specifically, the control unit 41 controls to display the second figure 72 at a frame rate of about 70% to 20% with respect to a frame rate at which the three-dimensional image 53 is displayed.

Alternatively, the control unit 41 of the image processing device 11 intentionally causes a delay in the second mode. For example, when the three-dimensional image 53 is updated at 30 FPS, the vibration is intense in the display in the second mode, which may cause a phenomenon that the display is difficult to see. Therefore, the control unit 41 limits a moving distance in the second mode. Specifically, the control unit 41 sets any distance as a maximum moving distance within, for example, a range of $\frac{1}{10}$ to $\frac{1}{1000}$ of a diameter of the lumen of the biological tissue 60. For example, it is assumed that a moving distance from a catheter position P[t] in the second mode at a certain time t to a catheter position P[t+1] in the second mode at a time t+1 after a unit time is longer than the maximum moving distance. In that case, the control unit 41 gradually moves the second figure 72 to reach, for example, the P[t+1] within 1 second (s) to 10 millisecond (ms) instead of moving the second figure 72 from the P[t] to the P[t+1] instantaneously. By this operation, a smooth movement can be implemented. However, if an actual catheter position is suddenly and significantly moved, inconsistency with reality may occur by using this method. Therefore, when the moving distance from the P[t] to the P[t+1] is extremely long, the control unit 41 instantaneously moves the second figure 72 from the P[t] to the P[t+1]. That is, the control unit 41 displays the catheter position as it is. That is, if a moving distance per unit time is less than the maximum moving distance or equal to or longer than a reference distance that is longer than the maximum moving distance, the control unit 41 displays the catheter position as it is without causing the delay. If the moving distance per unit time is equal to or longer than the maximum moving distance and less than the reference distance, the control unit 41 causes the delay.

In the first mode, the control unit 41 of the image processing device 11 may intentionally cause a frame rate delay only for the catheter 61. In the first mode, the first figure 71 is created in consideration of the past catheter positions, but calculation for creating the first figure 71 may be not within the update speed such as 30 FPS. Therefore, the control unit 41 may intentionally execute control to display the catheter position while reducing only the frame rate of the catheter position. For example, when the three-dimensional image 53 is updated at 30 FPS, the control unit 41 may execute control to display the first figure 71 at a frame rate, for example, slower than 30 FPS, such as 10 FPS.

As described above, in the modification, the control unit 41 of the image processing device 11 causes the display 16 to display the three-dimensional data 52 as the three-dimensional image 53, the three-dimensional data 52 representing the biological tissue 60. The control unit 41 separately constructs, from the tomographic data 51 obtained in time series by the ultrasound transducer 25 observing the surrounding of the lumen of the biological tissue 60 while moving in the lumen, three-dimensional biological tissue data representing the biological tissue 60, and first figure data representing the series of positions as a result of detection of the series of positions of the catheter 61 inserted into the biological tissue 60. The control unit 41 causes the display 16 to display the three-dimensional biological tissue data and the first figure data sequentially as the three-dimensional image 53 and the first figure 71, respectively. The control unit 41 controls such that an update speed of the first figure 71 is slower than an update speed of the three-dimensional image 53.

According to the modification, image display is not delayed even when the first figure 71 is not updated in time at the update speed of the three-dimensional image 53.

The present disclosure is not limited to the above-described embodiment. For example, a plurality of blocks described in the block diagram may be integrated, or one block may be divided. Instead of executing a plurality of steps described in the flowchart in time series according to the description, the steps may be executed in parallel or in a different order according to the processing capability of the device that executes each step or as necessary. In addition, modifications can be made without departing from a gist of the present disclosure.

The detailed description above describes embodiments of an image processing device, an image processing system, an image display method, and an image processing program. These disclosed embodiments represent examples of the image processing device, the image processing system, the image display method, and the image processing program. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image processing device configured to cause a display to display three-dimensional data as a three-dimensional image, the three-dimensional data representing a biological tissue, the image processing device comprising:
a control unit configured to:
generate the three-dimensional data based on tomographic data acquired by a sensor that is in a probe inserted into a lumen of the biological tissue, the sensor observing the surrounding of the lumen of the biological tissue while moving in the lumen;
detect a series of positions of a catheter inserted separately from the probe into the biological tissue from the tomographic data obtained in time series by the sensor while the sensor is moving in the lumen; and
switch a display mode between a first mode for displaying a first figure representing the series of positions in the three-dimensional image, and a second mode for displaying a second figure representing one position among the series of positions in the three-dimensional image.

2. The image processing device according to claim 1, wherein the control unit is configured to hide the first figure when the display mode is switched from the first mode to the second mode.

3. The image processing device according to claim 1, wherein the control unit is configured to display, as the first figure, a linear or tubular figure connecting the series of positions.

4. The image processing device according to claim 1, wherein the control unit is configured to display, as the second figure, a spherical figure representing the one position, and display at least one concentric circle or concentric sphere surrounding the spherical figure.

5. The image processing device according to claim 1, wherein the control unit is configured to display, as the second figure, a figure in which a thickness dimension on a side near an end of the catheter is larger than a thickness dimension on an opposite side.

6. The image processing device according to claim 5, wherein the control unit is configured to display, as the second figure, a bullet-shaped figure representing the one position.

7. The image processing device according to claim 1, wherein when displaying a figure representing a position other than a distal end of the catheter as the second figure, the control unit is configured to display the second figure in a color different from that when displaying a figure representing a position of the distal end of the catheter as the second figure.

8. The image processing device according to claim 1, wherein the control unit is configured to switch the display mode according to a change in a moving state of the sensor.

9. The image processing device according to claim 8, wherein the change in the moving state of the sensor includes a case in which a moving speed of the sensor exceeds a threshold value.

10. The image processing device according to claim 9, wherein when the moving speed of the sensor exceeds the threshold value, the control unit is configured to switch the display mode according to whether the moving speed of the sensor is equal to or less than an upper limit value.

11. The image processing device according to claim 1, wherein the control unit is configured to switch the display mode according to whether the catheter is present in an image plane captured by the sensor.

12. The image processing device according to claim 11, wherein when the catheter is present in the image plane, the control unit is configured to switch the display mode according to a magnitude of a movement of the catheter in the image plane.

13. The image processing device according to claim 11, wherein when the catheter is not present in the image plane, the control unit is configured to switch the display mode according to an elapsed time from a time point at which a last position among the series of positions is detected.

14. The image processing device according to claim 1, wherein in the second mode, the control unit is configured to adjust at least one of a size or a color of the second figure according to a distance from an inner wall surface of the biological tissue.

15. The image processing device according to claim 1, wherein in the second mode, the control unit is configured to adjust at least one of a size or a color of the second figure according to presence or absence of contact with the inner wall surface of the biological tissue.

16. The image processing device according to claim 1, wherein in the second mode, the control unit is further configured to display a shadow of the second figure.

17. The image processing device according to claim 1, wherein in the second mode, the control unit is configured to adjust an update frequency of the second figure associated with an update of the data.

18. An image processing system, comprising:
    the sensor configured to acquire the tomographic data of the biological tissue while moving in the lumen of the biological tissue; and
    the image processing device according to claim 1, the image processing device configured to generate the three-dimensional data based on the tomographic data acquired by the sensor.

19. The image processing system according to claim 18, further comprising:
    the display.

20. An image display method for causing a display to display three-dimensional data as a three-dimensional image, the three-dimensional data representing a biological tissue, the image display method comprising:
    generating, by a processor, the three-dimensional data based on tomographic data acquired by a sensor that is in a probe inserted into a lumen of the biological tissue, the sensor observing the surrounding of the lumen of the biological tissue while moving in the lumen;
    detecting, by the processor, a series of positions of a catheter inserted separately from the probe into the biological tissue from the tomographic data obtained in time series by the sensor while the sensor is moving in the lumen; and
    switching, by the processor, a display mode between a first mode for displaying a first figure representing the series of positions in the three-dimensional image, and a second mode for displaying a second figure representing one position among the series of positions in the three-dimensional image.

21. A non-transitory computer-readable medium (CRM) storing computer program code executed by a computer processor that executes an imaging process comprising:
    generating three-dimensional data representing a biological tissue based on tomographic data acquired by a sensor that is in a probe inserted into a lumen of the biological tissue, the sensor observing the surrounding of the lumen of the biological tissue while moving in the lumen;
    displaying, on a display, the three-dimensional data as a three-dimensional image;
    detecting a series of positions of a catheter inserted separately from the probe into the biological tissue from the tomographic data obtained in time series by the sensor while the sensor is moving in the lumen; and
    switching a display mode between a first mode for displaying a first figure representing the series of positions in the three-dimensional image, and a second mode for displaying a second figure representing one position among the series of positions in the three-dimensional image.

* * * * *